US011403507B2

(12) United States Patent
Malkevich et al.

(10) Patent No.: US 11,403,507 B2
(45) Date of Patent: Aug. 2, 2022

(54) SYSTEMS AND METHODS FOR MONITORING LAYER POULTRY HOUSES

(71) Applicant: YAN AGRO LOGIC (1988) LIMITED, Natanya (IL)

(72) Inventors: Genadi Malkevich, Natanya (IL); Anatoly Shirokov, Hadera (IL)

(73) Assignee: Yan Agro Logic (1988) Limited, Natanya (IL)

( * ) Notice: Subject to any disclaimer, the term of this patent is extended or adjusted under 35 U.S.C. 154(b) by 536 days.

(21) Appl. No.: 16/480,227

(22) PCT Filed: Jan. 21, 2018

(86) PCT No.: PCT/IL2018/050073
§ 371 (c)(1),
(2) Date: Jul. 23, 2019

(87) PCT Pub. No.: WO2018/154556
PCT Pub. Date: Aug. 30, 2018

(65) Prior Publication Data
US 2020/0005115 A1    Jan. 2, 2020

(30) Foreign Application Priority Data

Feb. 27, 2017    (IL) .......................................... 250809

(51) Int. Cl.
*G06M 11/00* (2006.01)
*G01N 33/08* (2006.01)
(Continued)

(52) U.S. Cl.
CPC ............. *G06M 11/00* (2013.01); *G01N 21/84* (2013.01); *G01N 33/08* (2013.01); *G06M 1/101* (2013.01);
(Continued)

(58) Field of Classification Search
CPC ...... G06M 11/00; G06M 11/02; G06M 11/04; G06M 1/101; G06M 7/00; G06M 7/02; G06M 7/04
(Continued)

(56) References Cited

U.S. PATENT DOCUMENTS 4,528,680 A    7/1985   Archambeault
4,868,901 A    9/1989   Kniskern et al.
(Continued)

FOREIGN PATENT DOCUMENTS

CN    204904322    12/2015
EP    1856971      11/2007
(Continued)

OTHER PUBLICATIONS

Extended European Search Report, European Application No. 18758286, dated Mar. 3, 2020.
(Continued)

*Primary Examiner* — Hai L Nguyen
(74) *Attorney, Agent, or Firm* — The Roy Gross Law Firm, LLC; Roy Gross

(57) ABSTRACT

Systems and methods for monitoring poultry house egg production. The system includes: a conveyor for conveying poultry eggs; at least one laser sensor directed in direction of said conveyor for measuring distance of said conveyor's surface and poultry eggs conveyed thereupon; a computer coupled with said at least one lase sensor; wherein, number of poultry eggs passed through said conveyor at a given moment is determined by identifying and analyzing fluctuations in measured distance from said at least one laser sensor.

7 Claims, 4 Drawing Sheets

(51) Int. Cl.
*G06M 1/10* (2006.01)
*G01N 21/84* (2006.01)
*G06M 7/00* (2006.01)
*A01K 43/00* (2006.01)

(52) U.S. Cl.
CPC ............... *G06M 7/00* (2013.01); *A01K 43/00* (2013.01); *G01N 2021/845* (2013.01)

(58) Field of Classification Search
USPC ........................................................ 377/3, 6
See application file for complete search history.

(56) References Cited

U.S. PATENT DOCUMENTS 7,878,391 B2 * 2/2011 Kalkhoff ............... A01K 43/00
235/98 C
7,950,349 B1 5/2011 Rollins
2014/0261189 A1 9/2014 Chait

FOREIGN PATENT DOCUMENTS

| FR | 2812086 | 1/2002 |
| FR | 2812086 A1 | 1/2002 |
| GB | 2226130 | 6/1990 |
| JP | 2003346124 | 12/2003 |
| JP | 2004013857 | 1/2004 |
| WO | 0207086 | 1/2002 |

OTHER PUBLICATIONS

IL Search Report for IL 250809 dated Apr. 2, 2017.
International Search Report PCT/IL2018/050073 Completed Apr. 26, 2018; dated Apr. 29, 2018 3 pages.
Written Opinion of the International Searching Authority PCT/IL2018/050073 dated Apr. 29, 2018 5 pages.

* cited by examiner

SYSTEMS AND METHODS FOR MONITORING LAYER POULTRY HOUSES

RELATED APPLICATIONS

This application is a National Phase of PCT Patent Application No. PCT/IL2018/050073 having International filing date of Jan. 21, 2018, which claims the benefit of priority of Israeli Patent Application No. 250809 filed on Feb. 27, 2017. The contents of the above applications are all incorporated by reference as if fully set forth herein in their entirety.

FIELD OF THE INVENTION

The present invention relates generally to the field of systems and methods for monitoring layer poultry houses.

BACKGROUND OF THE INVENTION

Layer poultry farms and more specifically, layer poultry houses are controlled habitats for raising domesticated birds such as chicken, ducks, and geese, for egg production purposes.

Poultry farms are typically divided to several areas. Each area contains dwelling cages where birds dwell at least some part of the day. When laid, eggs are directed to processing by specialized conveyors.

It is generally understood that any layer poultry houses require counting the amount of eggs produced in the farm to monitor the productivity of the poultry house. Additionally, since a decrease in egg output is an indication to bird health problems, there is a need to monitor and analyze egg production.

It is also understood that due to the large egg volume processed in an industrial poultry house, manual egg counting is not viable. Therefore, several attempts have been made to provide an automated system for counting eggs in poultry houses.

Systems involving video cameras and visual recognition algorithms were attempted as means for monitoring poultry house egg production. Such attempts have several important drawbacks.

Firstly, visual recognition algorithms suffer from relatively high runtime complexity.

Secondly, pre-configuration of such a system is rather complex since every system should be adapted to various egg sizes and shapes.

Thirdly, visual recognition is inaccurate where there is insufficient contrast between egg and conveyor.

Systems involving infrared active sensor array were also attempted for this purpose. Such systems have the following drawbacks:

Firstly, intensity of returning IR radiation depends on the material, shape, and color of the object, therefore, such a system shall be inaccurate when scanning eggs of various sizes and colors, and where the eggs are covered by feathers and droppings.

Secondly, in some situations for example when eggs are covered by feathers and droppings, the conveyor reflectance may be higher than egg reflectance, resulting in low counting accuracy.

Considering the above description of the current state of the art, it is clear that there is a long-standing need for a system for monitoring poultry house egg production, that overcomes the following shortcomings:

a. Dependency on characteristics such as egg shape and size, contrast and relative reflectance between egg and conveyor belt.
b. High algorithm runtime complexity and complex setup process.

SUMMARY OF THE INVENTION

The present invention relates to systems and methods for monitoring poultry house egg production. The system of the present invention is comprised of the following:

a. a conveyor for conveying poultry eggs;
b. at least one laser sensor directed in direction of said conveyor for measuring distance of said conveyor's surface and poultry eggs conveyed thereupon;
c. a computer coupled with said at least one laser sensor;

wherein, number of poultry eggs passed through said conveyor at a given moment is determined by identifying a compliant pattern in analyzed fluctuations over time of measured distance from said at least one laser sensor.

It is within the provision of the present invention that identifying a compliant pattern is performed by identifying minima of said measured distance, such that each minimum in distance considered as a single poultry egg.

It is within the provision of the present invention that identifying a compliant pattern is performed by identifying an oval shape of an egg in said measured distance over time, such that each fluctuation of distance over time that resembles an oval shape is considered as a single poultry egg.

The present invention provides many advantages over the prior art, among others, the following:

a. There is no dependency on characteristics such as egg shape and size, contrast and relative reflectance between egg and conveyor belt. The system identifies poultry eggs by measuring distance and identifying fluctuations in distance.
b. Low algorithm runtime complexity and no need for system setup. The present invention allows identifying poultry eggs without using expensive visual recognition algorithms.

BRIEF DESCRIPTION OF THE DRAWINGS

Embodiments and features of the present invention are described herein in conjunction with the following drawings.

DETAILED DESCRIPTION OF PREFERRED EMBODIMENTS

The present invention will be understood from the following detailed description of preferred embodiments, which are meant to be descriptive and not limiting. For the sake of brevity, some well-known features, methods, systems, procedures, components, circuits, and so on, are not described in detail.

Figure 1:
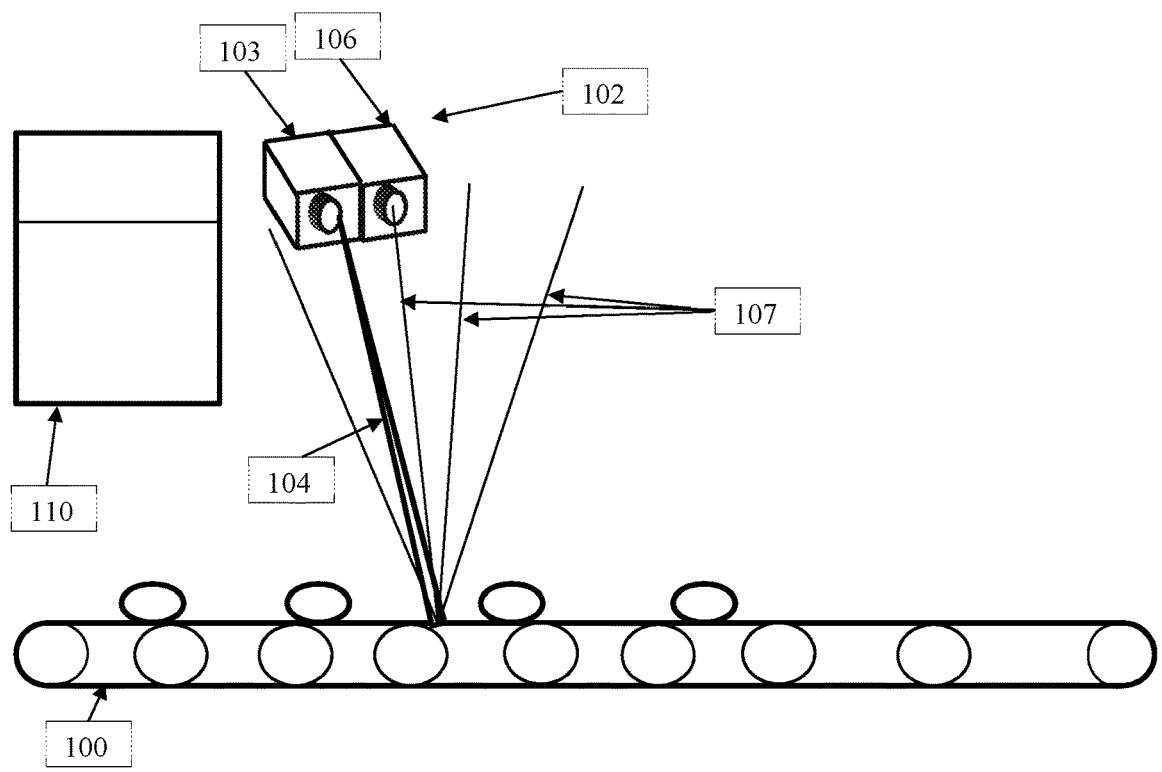
FIG. 1 is a diagram depicting a system of the present invention.
Figure 2:
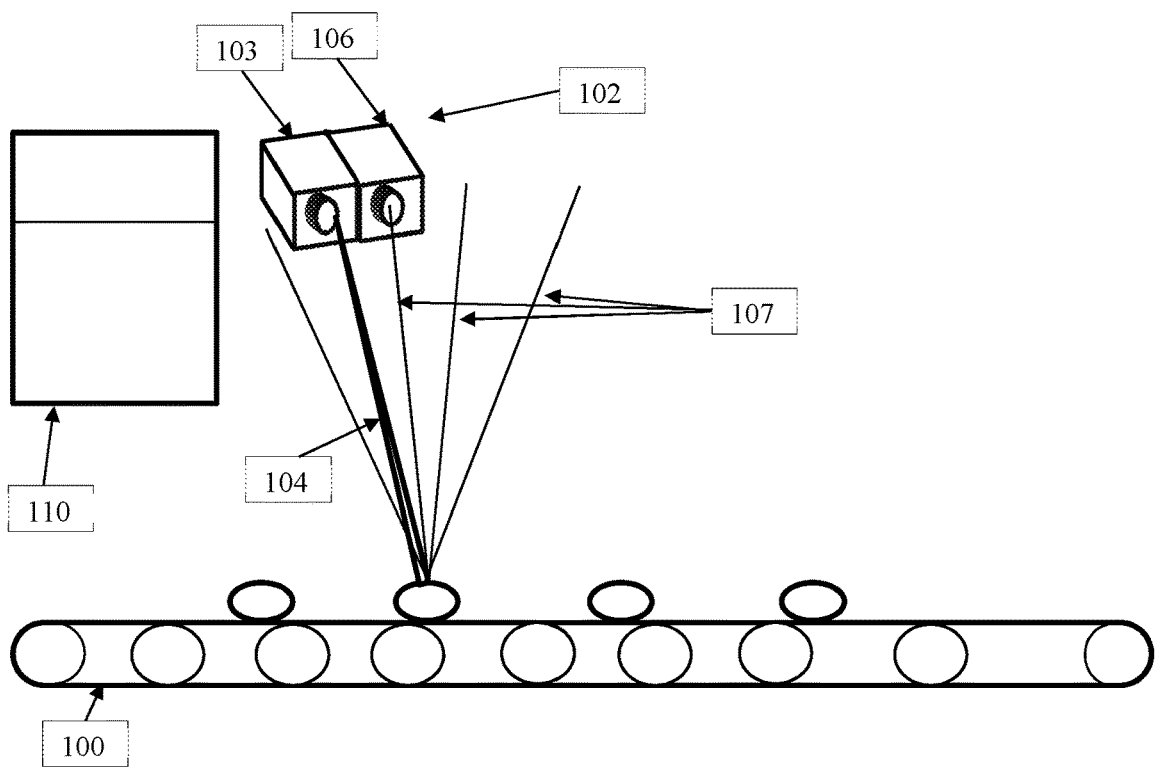
FIG. 2 is diagram depicting a system of the present invention.
Figure 3:
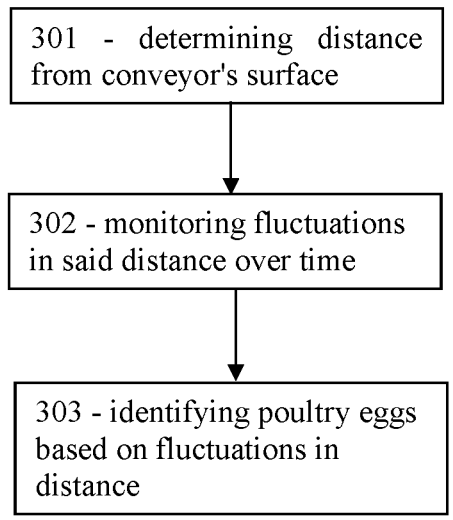
FIG. 3 is a flowchart of a method of the present invention.

FIG. 1 depicts a system for monitoring poultry house egg production comprising:
  a. a conveyor 100 for conveying poultry eggs;
  b. at least one laser sensor 102 directed in direction of said conveyor;
    As can be seen, the laser sensor in this embodiment is an active sensor, comprising a transmitter 103 for transmitting monochromatic light pulses 104 and a receiver 106 for capturing reflected light rays 107.
  c. a computer coupled with said at least one lase sensor 110;

FIG. 2 depicts the system depicted in FIG. 1. This time the light transmitted from the active laser sensor 102 is reflected from a poultry egg and not from the conveyor 100 itself FIG. 3 illustrates a method for monitoring poultry house egg production. The method is comprised of the following steps:
  a. determining distance from conveyor's surface 301;
  b. monitoring fluctuations in said distance over time 302;
    This step is preferably performed by recording in a memory of said computer values of distance from said conveyor over time.
  c. identifying poultry eggs based on fluctuations in distance such that each fluctuation in distance is considered as a single poultry egg 303.

Figure 4:
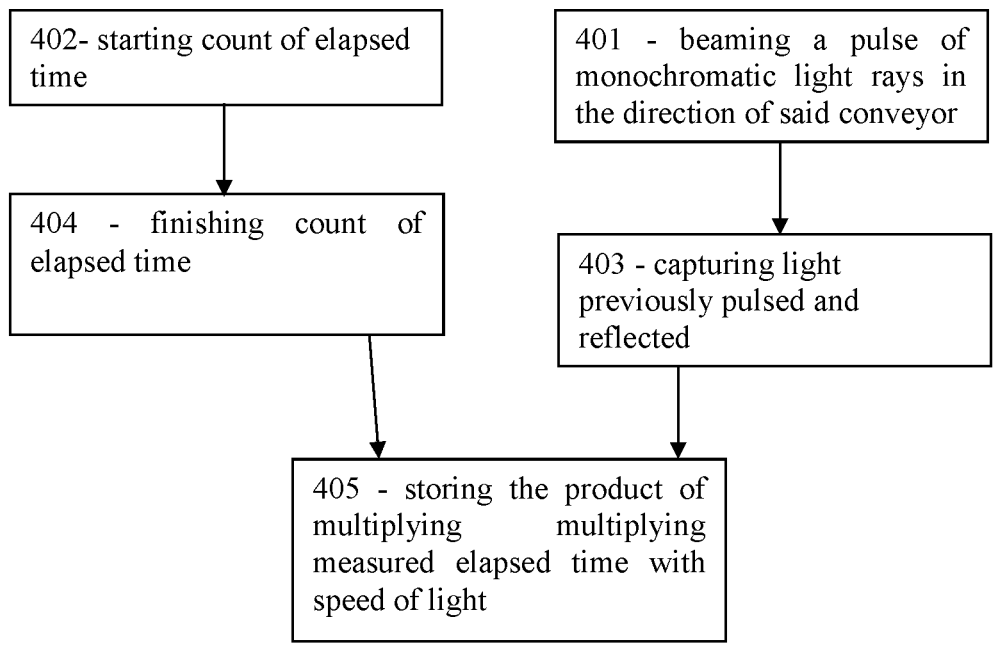
FIG. 4 is a flowchart of a method of the present invention.

FIG. 4 illustrates a method illustrates a method for determining distance from a conveyor. The method is comprised of the following steps:
  a. beaming a pulse of monochromatic light rays in the direction of said conveyor 401;
    For this purpose, an active laser sensor, comprising a both a transmitter and a receiver, is preferably used. Such a sensor is capable of both pulsing monochromatic light and capturing reflected pulsed light.
  b. starting count of elapsed time from the moment of beaming said pulse of light 402;
  c. capturing light previously pulsed and reflected from said conveyor or from poultry eggs laid thereupon 403;
  d. finishing count of elapsed time at the moment of capturing reflected light 404;
  e. storing a value of distance from conveyor which is a product of multiplying of measured elapsed time with speed of light in memory of said computer 405.

Figure 5:
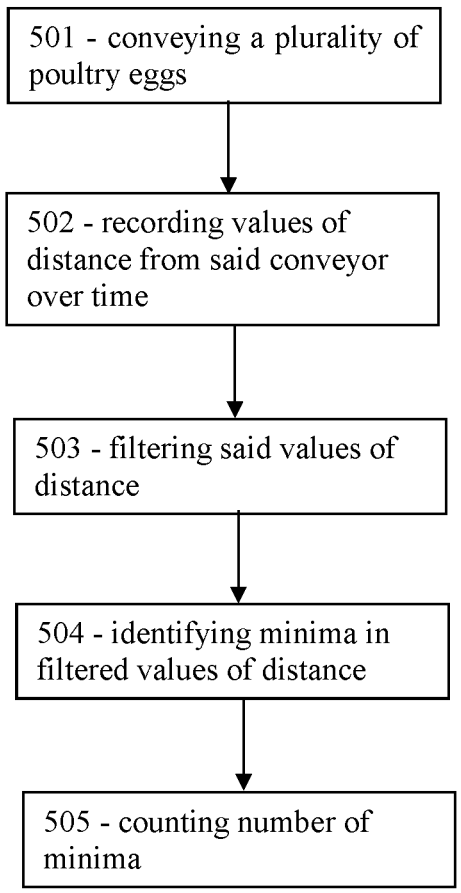
FIG. 5 is a flowchart of a method of the present invention.

FIG. 5 illustrates an exemplary method for identifying poultry eggs based on fluctuations in distance, comprising steps of:
  a. conveying a plurality of poultry eggs upon said conveyor 501;
  b. recording in a memory of said computer values of distance from said conveyor over time 502;
  c. filtering said values of distance recorded in said memory of said computer 503;
    For this purpose, a data filtering algorithm such as the Savitzky-Golay filter, may be used.
  d. identifying minima in filtered values of distance 504;
  e. counting number of minima of distance values 505;
wherein, each minimum is considered as a counted poultry egg.

Figure 6:
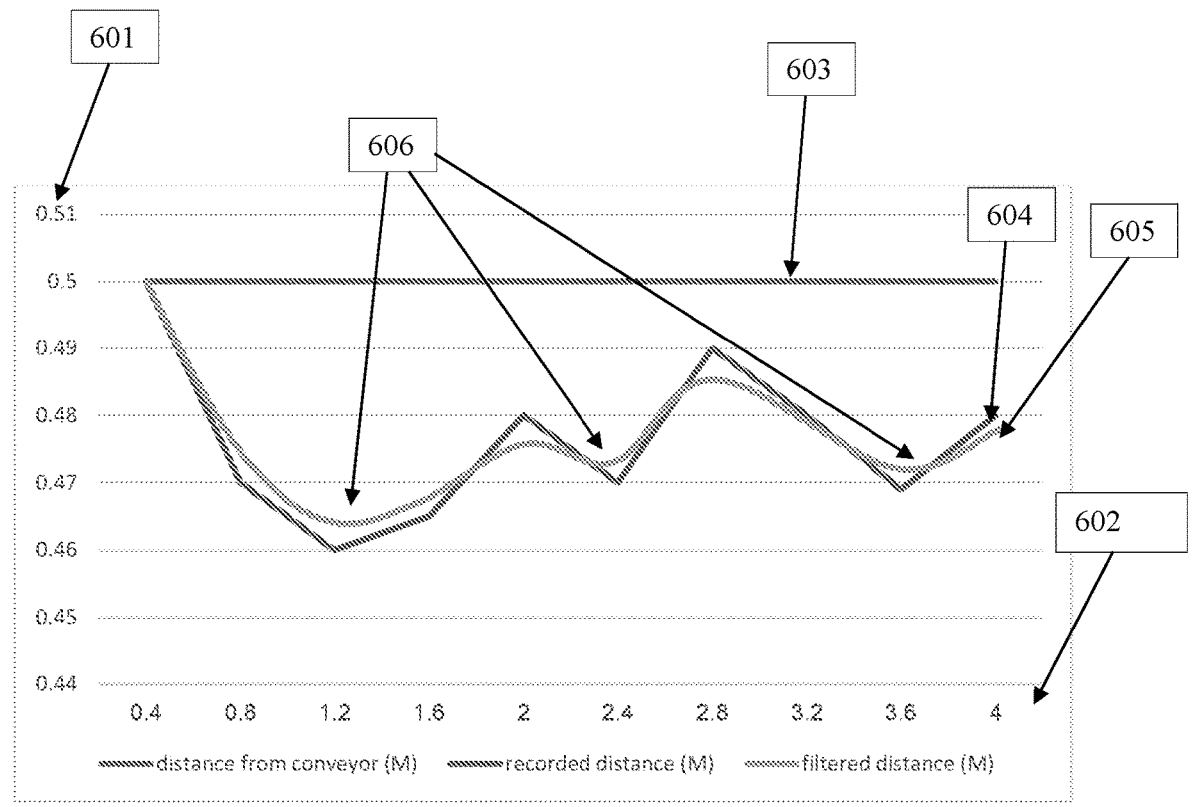
FIG. 6 is a chart of readings created by an embodiment of the present invention.

FIG. 6 is a chart presenting values of distance 601 in meters, over time 602 in seconds.

603 is value of distance from the conveyor itself. As can be seen this value is fixed and determined at the initialization of a system of the present invention.

604 is a graph of all recorded values of actual distance over time. The values are recorded at certain intervals. In this instance, values were recoded over a time frame of 4 seconds.

605 is a graph with smoothed values undergone filtering.

606 are 3 detected smoothed minima. In this instance, the system counted 3 poultry eggs conveyed by the conveyor at the sampled time frame.

The foregoing description and illustrations of the embodiments of the invention has been presented for the purposes of illustration. It is not intended to be exhaustive or to limit the invention to the above description in any form.

Any term that has been defined above and used in the claims, should be interpreted according to this definition.

The invention claimed is:

1. A system for monitoring poultry house egg production, comprising:
  at least one laser sensor directed in direction of a conveyor for measuring distance from said conveyor's surface and poultry eggs conveyed thereupon to said laser sensor;
  a computer coupled with said at least one laser sensor;
  wherein, processing circuitry of said computer is configured to perform the steps comprising:
  register a poultry egg by identifying a compliant pattern in fluctuations over time of measured distance from said at least one laser sensor, wherein calculating distance to said at least one laser sensor is performed by counting elapsed time from moment of beaming of a light pulse from said at least one laser sensor to a moment of capturing reflected light.

2. The system of claim 1, wherein processing circuitry of said computer is further configured to identify minima of said measured distance as said compliant pattern, such that each minimum in distance is considered as a single poultry egg.

3. The system of claim 1, wherein processing circuitry of said computer is further configured to identify an oval shape of an egg in said measured distance over time as said compliant pattern, such that each fluctuation of distance over time that resembles an oval shape is considered as a single poultry egg.

4. A method for monitoring poultry house egg production, comprising the steps of:
  a. determining distance to at least one laser sensor directed in direction of said conveyor and a computer having processing circuitry configured to register a poultry egg by identifying a compliant pattern in fluctuations over time of measured distance from said at least one laser sensor;
  b. monitoring fluctuations in said distance over time by recording in a memory of a computer values of distance from said conveyor over time;
  c. identifying poultry eggs based on fluctuations in distance such that each fluctuation in distance that is compliant, shall be considered as a single poultry egg.

5. The method of claim 4, wherein monitoring fluctuations in distance over time is executed with a method, comprising the steps of:
  a. beaming a pulse of monochromatic light rays in the direction of said conveyor with said at least one laser sensor;
  b. starting count of elapsed time from the moment of beaming said pulse of light;
  c. capturing light previously pulsed and thereafter reflected from said conveyor and from poultry eggs laid thereupon;
  d. finishing count of elapsed time at the moment of capture of reflected light;

e. storing a value of distance from conveyor which is a product of multiplying of measured elapsed time with speed of light in memory of said computer.

6. The method of claim 4, wherein identifying poultry eggs based on fluctuations in distance is executed with a method, comprising the steps of:
  a. conveying a plurality of poultry eggs upon a conveyor;
  b. recording in a memory of said computer values of distance from said conveyor over time;
  c. filtering said values of distance recorded in said memory of said computer;
  d. identifying minima in filtered values of distance;
  e. counting number of minima of distance values;
  wherein, each minimum is considered as a compliant fluctuation in distance and counted as a poultry egg.

7. The method of claim 4, wherein identifying poultry eggs based on fluctuations in distance is executed with a method, comprising the steps of:
  a. conveying a plurality of poultry eggs upon a conveyor;
  b. recording in a memory of said computer values of distance from said conveyor over time;
  c. filtering said values of distance recorded in said memory of said computer;
  d. identifying a shape that resembles an oval shape of an egg in filtered values of distance;
  e. counting number of identified shapes;
  wherein, each shape that resembles an oval shape of an egg is considered as a compliant fluctuation in distance and counted as a poultry egg.

* * * * *